United States Patent [19]

Mazzuchelli et al.

[11] Patent Number: 5,155,255
[45] Date of Patent: Oct. 13, 1992

[54] PROCESS FOR PRODUCING CYCLOALKENYLALKENES

[75] Inventors: Mario Mazzuchelli, Basel; Milan Soukup, Stein; Paul Spurr; Claude Stritt, both of Basel, all of Switzerland

[73] Assignee: Hoffmann-La Roche Inc., Nutley, N.J.

[21] Appl. No.: 673,909

[22] Filed: Mar. 25, 1991

[30] Foreign Application Priority Data

Apr. 27, 1990 [CH] Switzerland .......................... 1443/90

[51] Int. Cl.$^5$ ............................................ C07C 403/12
[52] U.S. Cl. ...................................... 560/260; 560/105
[58] Field of Search ...................... 560/259, 260, 105

[56] References Cited

PUBLICATIONS

Isler et al., Helv.Chim. Acta., 32:489-499 (1949).
Isler et al., Helv.Chim. Acta., 39:249-259 (1956).
Isler et al., Helv.Chim. Acta., 51:447-462 (1979).

Primary Examiner—Jose G. Dees
Attorney, Agent, or Firm—George M. Gould; William H. Epstein; Catherine R. Roseman

[57] ABSTRACT

A process for the manufacture of certain cycloalkenylalkenes, e.g. vitamin A acetate, comprises dehydrating 1-(5-acetoxy-3-methyl-penta-1,3-dienyl)-2,6,6-trimethyl-cyclo hexanol or 4 aetoxy-1-(5-acetoxy-3-methyl-penta-1,3-dienyl)-2,6,6-trimethyl-cyclohexanol or 1-(9-acetoxy-3,7-dimethyl-4-hydroxy-nona-2,5,7-trienyl)-2,6,6-trimethyl- cyclohexene in the presence of an alkali metal bromide or of manganese bromide or of a hydrate of such a bromide as the catalyst and in an organic solvent.

The products are especially suitable as intermediates in carotinoid syntheses.

18 Claims, No Drawings

PROCESS FOR PRODUCING CYCLOALKENYLALKENES

SUMMARY OF INVENTION

The present invention is concerned with a novel process for the manufacture of cycloalkenylalkenes having a through-conjugated structure, which are especially suitable as intermediates in carotinoid syntheses.

DETAILED DESCRIPTION

The process in accordance with the invention comprises dehydrating 1-(5-acetoxy-3-methyl-penta-1,3-dienyl)-2,6,6-trimethyl-cyclohexanol Ia or 4-acetoxy-1-(5-acetoxy-3-methyl-penta-1,3-dienyl)-2,6,6-trimethyl-cyclohexanol Ib or 1-(9-acetoxy-3,7-dimethyl-4-hydroxy-nona-2,5,7-trienyl)-2,6,6-trimethyl-cyclohexene Ic in the presence of an alkaline earth metal bromide or of manganese bromide or of a hydrate of such a bromide as the catalyst and in an organic solvent.

This process is illustrated by the following Reaction Scheme

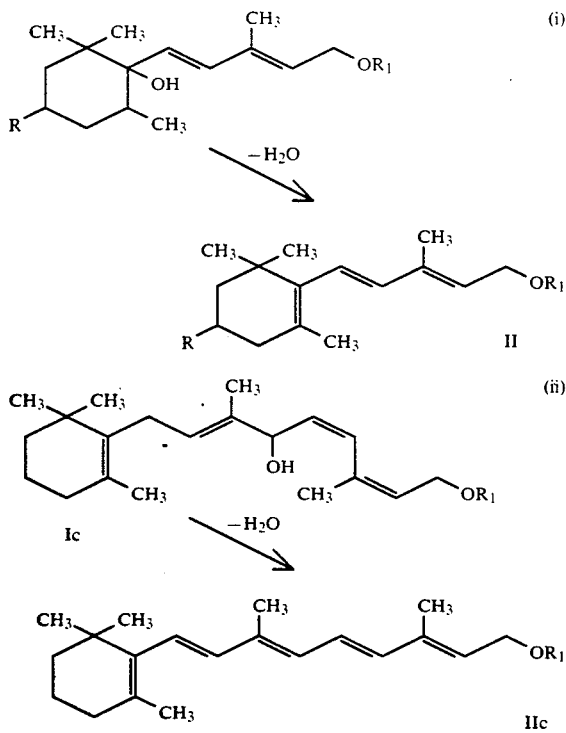

wherein R is H or OR$_1$; and R$_1$ taken together with its attached oxygen atom forms a hydrolyzable ester protecting group.

It has been found that the process in accordance with the invention is economical, especially as byproducts and waste products which are difficult to remove and to eliminate can be avoided and, compared with previously used dehydration processes, the process proceeds with good yield using only 5–10 mol percent of catalyst.

In accordance with this invention R$_1$ can be any conventional group which forms a hydrolyzable ester group, R$_1$ being particularly acyl, more particularly acetyl.

Exemplarly ester groups useful for this purpose are those in which the acyl moiety is derived from a lower alkanoic or an aryl lower alkanoic acid. Among the reagents which can be utilized to form such ester groups are the acid anhydrides and the acid halides, preferably chlorides, with the lower alkanoic acid anhydrides, e.g., acetic anhydride, being particularly preferred.

In accordance with this invention any conventional inert organic solvent can be used in carrying out the dehydration reaction.

Suitable organic solvents for carrying out the process in accordance with the invention are nitriles, e.g. acetonitrile; ketones, e.g. acetone; as well as esters, e.g. methyl acetate or isopropenyl acetate. Acetonitrile, acetone and isopropenyl acetate are the preferred solvents. Suitable catalysts in hydrate form are, for example, calcium bromide dihydrate CaBr$_2$.2H$_2$O), magnesium bromide hexahydrate (MgBr$_2$.6H$_2$O), manganese bromide tetrahydrate (MnBr$_2$.4H$_2$O) and strontium bromide hexahydrate (SrBr$_2$.6H$_2$O). Calcium bromide, magnesium bromide and manganese bromide as well as hydrates thereof (especially CaBr$_2$.2H$_2$O and MgBr$_2$.6H$_2$O) are preferred catalysts.

Under alkaline earth metal bromides there are to be understood magnesium bromide, calcium bromide, strontium bromide and barium bromide, of which magnesium bromide, calcium bromide and strontium bromide, especially the first two, are preferred.

In fact any conventional alkaline earth metal bromides can be utilized in the process of this invention.

In order to achieve optimum reaction conditions, the choice of the catalyst generally depends on the solvent to be used, i.e. certain catalyst/solvent combinations are especially advantageous in the process in accordance with the invention. CaBr$_2$.2H$_2$O/acetonitrile, CaBr$_2$.2H$_2$O/acetone and MgBr$_2$.6H$_2$O/isopropenyl acetate are especially preferred catalyst/solvent combinations.

The amount of catalyst used also substantially influences the course of the process in accordance with the invention. In general, the required amount of catalyst amounts to 4 to 40 mol percent based on the amount of educt Ia, Ib or Ic used.

The optimum reaction temperature depends on various factors, inter alia on the nature of the solvent used, but generally lies in the range of about −20° C. to about 50° C., with the dehydration of Ia or Ib being preferably effected at the higher temperatures in this range, that of Ic on the other hand being preferably effected at the lower temperatures. When Ic is dehydrated in acetonitrile as the solvent, the process is preferably carried out at about 0° C., while the reaction temperature in the case of this dehydration in acetone is preferably room temperature. In both cases the reaction time is advantageously from 2 to 7 hours.

In order to increase the activity of the respective catalyst, the process in accordance with the invention is carried out with the addition of an amino acid hydrobromide such as, for example, glycine hydrobromide, anthranilic acid hydrobromide, lysine hydrobromide or β-alanine hydrobromide, preferably the lastnamed. The amount of amino acid hydrobromide conveniently amounts to 1 to 10 mol percent, preferably 1 to 4 mol percent, based on the amount of educt. A molar ratio of about 1:1 calcium bromide dihydrate and β-alanine hydrobromide has been found to be especially advantageous for the dehydration.

When calcium bromide or its dihydrate is used as the catalyst, the presence of a small amount of acetic acid has been found to be especially advantageous for the dehydration. Very good yields are obtained, for example, by using about 40 mol percent of calcium bromide dihydrate in acetonitrile together with a trace of acetic acid at about 0° C., with the optimum reaction time lying at about 5 hours.

As an alternative to the enhancement of the activity of calcium bromide or of its dihydrate as the catalyst by the addition of an amino acid hydrobromide or of acetic acid, the process in accordance with the invention can be carried out with the addition of an earth, e.g. montmorillonite, a polymeric acid, e.g. polymethacrylic acid, or of the hydrobromide salt of a polymer-bound amino acid, e.g. polyvinylphenylalanine hydrobromide, or of calcium glutamate, or of glutamic acid or aspartic acid. In all instances except where an earth is used, the dehydration is conveniently effected in the presence of acetonitrile as the solvent at room temperature. When an earth is used, the dehydration is conveniently effected in the presence of acetonitrile at temperatures up to about 0° C. The molar amount of the additive conveniently corresponds to about that of the catalyst and preferably lies in the lower part of the range of 4-40 mol percent based on the amount of educt used, especially about 4 mol percent.

An especially preferred embodiment of the process in accordance with the invention comprises dehydrating 1-(9-acetoxy-3,7-dimethyl-4-hydroxy-nona-2,5,7-trienyl)-2,6,6-trimethyl-cyclohexene in the presence of calcium bromide dihydrate and β-alanine hydrobromide in a molar ratio of about 1:1 either in acetonitrile at about 0° C. or in acetone at room temperature.

The starting materials Ia, Ib and Ic are known compounds. The 1-(9-acetoxy-3,7-dimethyl-4-hydroxy-nona-2,5,7-trienyl)-2,6,6-trimethyl-cyclohexene (Ic) can be produced, for example, together with a much smaller amount of the corresponding diacetate 1-(4,9-diacetoxy-3,7-dimethyl-nona-2,5,7-trienyl)-2,6,6-trimethyl-cyclohexene from hydroxenin [1-(4,9-dihydroxy-3,7-dimethyl-nona-2,5,7-trienyl)-2,6,6-trimethyl-cyclohexene] by trans-esterification with methyl acetate or by acetylation with acetic anhydride. The product of this acetylation usually consists of an 85:15 to 92:8 mixture of the monoacetate (Ic) and the diacetate. The diacetate can likewise be converted into the compound of formula IIc by the process in accordance with the invention, but the reaction velocity is substantially slower than that when the monoacetate is used.

The dehydration product of formula IIa or IIb is suitable as an intermediate for the manufacture of vitamin A, β-carotene or zeaxanthin, while the dehydration product of formula IIc is vitamin A acetate.

The invention is illustrated by the following Examples.

EXAMPLE 1

Manufacture of 4-acetoxy-1-(5-acetoxy-3-methyl-penta-1(E),3(E)-dienyl)-2,6,6-trimethyl-cyclohexene (IIb)

A solution of 34.2 g of 4-acetoxy-1-(5-acetoxy-3-methyl-penta-1(E),3(E)-dienyl)-2,6,6-trimethyl-cyclohexanol (99% purity according to gas chromatography; 100 mmol) in 160 ml of isopropenyl acetate (1470 mmol) is treated with 1.46 g of magnesium bromide hexahydrate (5 mmol) under argon and while stirring and the mixture is heated at reflux temperature (oil bath temperature 130°–135° C., internal temperature 95°–97° C.) for 15.5 hours while stirring vigorously (500 r/min.). The course of reaction is followed by gas chromatography. Subsequently, the mixture is cooled to room temperature and treated with 5 ml of triethylamine (36 mmol) and 500 ml of toluene. Then the mixture is concentrated at 40° C. under reduced pressure (waterjet vacuum), the oily residue is dissolved in 400 ml of toluene and the organic solution is washed twice with 400 ml of saturated sodium bicarbonate solution each time. The aqueous phases are extracted twice with 400 ml of toluene each time. The organic phases are combined, dried over anhydrous sodium sulphate and filtered, and the filtrate is evaporated at about 40° C. under reduced pressure and subsequently the residue is dried under a high vacuum for about 2 hours.

In this manner there are obtained about 40.0 g of 4-acetoxy-1-(5-acetoxy-3-methyl-penta-1(E),3(E)-dienyl)-2,6,6-trimethyl-cyclohexene; purity according to gas chromatography about 71.2 percent. This crude product can be processed immediately, e.g. as an intermediate for the manufacture of zeaxanthin.

EXAMPLE 2

Manufacture of 1-(9-acetoxy-3,7-dimethyl-nona-1(E),3(E),5(E),7(E)-tetraenyl)-2,6,6-trimethyl-cyclohexene (IIc) (1st variant)

34.45 g of a mixture of 1-(9-acetoxy-3,7-dimethyl-4-hydroxy-nona-2(E),5(Z),7-trienyl)-2,6,6-trimethyl-cyclohexene (Ic) and 1-(4,9-diacetoxy-3,7-dimethyl-nona-2(E),5(Z),7(Z)-trienyl)-2,6,6-trimethyl-cyclohexene (Id) (99 mmol; molar ratio Ic:Id about 85:15) are dissolved in 600 ml of acetonitrile. To the solution, cooled to 0° C., are added 0.48 g of calcium bromide dihydrate (2 mmol) as well as 0.34 g of β-alanine hydrobromide (2 mmol) and the mixture is stirred for about 3 hours. The course of the reaction is followed by thin-layer chromatography until it is established that almost no traces of the starting material remain.

Subsequently, 300 ml of semi-saturated sodium bicarbonate solution and 150 ml of methylene chloride are added to the reaction mixture. The organic phase is extracted three times with 100 ml of methylene chloride each time and the combined organic phases are dried with 50 g of anhydrous sodium sulphate. After filtering off the drying agent and washing it with 100 ml of methylene chloride the filtrate is evaporated under reduced pressure at a bath temperature of 40° C. The residue is dried to constant weight for 30 minutes at 45° C./0.5 mmHg. In this manner there are obtained 32.3 g of a mixture of 1-(9-acetoxy-3,7-dimethyl-nona-1(E),3(E),5(E),7(E)-tetraenyl)-2,6,6-trimethyl-cyclohexene (IIc, vitamin A acetate) and the corres- ponding 13-cis isomer ("13-cis") as a yellow syrup.

| Analysis (HPLC): | |
| --- | --- |
| IIc | 64.7% |
| 13-cis | 11.5% |

The crude product (IIc+13-cis) is dissolved in 55 ml of a solvent mixture pre-prepared from 95 ml of methanol, 5 ml of methylene chloride and 0.1 ml of pyridine. The solution is seeded with pure IIc and stirred at −25° C. for 16 hours. Subsequently, the resulting crystals are filtered off and washed twice with 12 ml of pre-cooled (−25° C.) methanol each time and dried at 35° C./40 mmHg for 30 minutes. In this manner there is obtained 1-(9-acetoxy-3,7-dimethyl-nona-1(E),3(E),5(E),7(E)- tetraenyl)-2,6,6-trimethyl-cyclohexene (IIc) in purer form (with about 5-10 mol percent of the 13-cis isomer).

| Analysis (HPLC): | |
|---|---|
| IIc | 91.0% |
| 13-cis | 7.6% |

EXAMPLE 3

Manufacture of 1-(9-acetoxy-3,7-dimethyl-nona-1(E),3(E),5(E),7(E)-tetraenyl)-2,6,6-trimethyl-cyclohexene (IIc) (2nd variant)

34.45 g of a mixture of 1-(9-acetoxy-3,7-dimethyl-4-hydroxy-nona-2(E),5(Z),7(Z)-trienyl)-2,6,6-trimethyl-cyclohexene (Ic) and 1-(4,9-diacetoxy-3,7-dimethyl-nona-2(E),5(Z),7(Z)-trienyl)-2,6,6-trimethyl-cyclohexene (Id) (100 mmol; molar ratio Ic:Id about 85:15) are dissolved in 600 ml of acetone. The solution is stirred at room temperature and 0.96 g of calcium bromide dihydrate (4 mmol) as well as 0.68 g of β-alanine hydrobromide (4 mmol) are added thereto. The reaction mixture is subsequently stirred for about 4 hours.

Thereafter, 32.9 g of a mixture of 1-(9acetoxy-3,7-dimethyl-nona-1(E),3(E),5(E),7(E)-tetraenyl)-2,6,6-trimethyl-cyclohexene (IIc, vitamin A acetate) and the corresponding 13-cis isomer ("13-cis") are isolated from the mixture as a yellow syrup using the same working-up method as described in the second paragraph of Example 2.

| Analysis (HPLC): | |
|---|---|
| IIc | 51.7% |
| 13-cis | 15.1% |

The crystallization method which is described in the third paragraph of Example 2 is also carried out in this case and there is obtained in this manner 1-(9-acetoxy-3,7-dimethyl-nona-1(E),3(E),5(E),7(E)-tetraenyl)-2,6,6-trimethyl-cyclohexene (IIc) in pure form (with a smaller amount of 13-cis).

| Analysis (HPLC): | |
|---|---|
| IIc | 82.6% |
| 13-cis | 7.5% |

We claim:

1. The process for producing a compound of the formula:

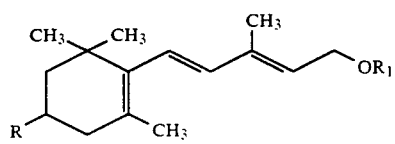

wherein R is H or OR₁; and R₁ taken together with its attached oxygen atom forms a hydrolyzable ester protecting group; comprising dehydrating in an organic solvent a cyclohexanol compound of the formula:

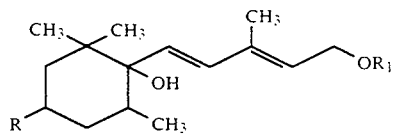

wherein $R_1$ is as above; in the presence of a catalyst selected from the group consisting of an alkaline earth metal bromide, manganese bromide and hydrates thereof, and optionally in the presence of an amino acid hydrobromide.

2. The process of claim 1, wherein the catalyst is calcium bromide, calcium bromide dihydrate, magnesium bromide, magnesium bromide hexahydrate or manganese bromide.

3. The process of claim 1, wherein the solvent is acetonitrile, acetone or isopropenyl acetate.

4. The process of claim 1, wherein the amount of catalyst used is 4 to 40 mol percent based on the amount of compound to be dehydrated.

5. The process of claim 1, wherein the dehydration is carried out in the temperature range of −20° C. to 50° C.

6. The process of claim 1, wherein the dehydration is carried out in the presence of the amino acid hydrobromide β-alanine hydrobromide.

7. The process of claim 6, wherein the amount of β-alanine hydrobromide is 1 to 4 mol percent based on the amount of said cyclohexanol.

8. The process of claim 1, wherein the dehydration is effected in the presence of about 40 mol percent of calcium bromide dihydrate in acetonitrile together with a trace of acetic acid at about 0° C.

9. The process for producing a compound of the formula:

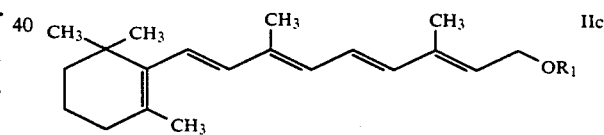

wherein $R_1$ taken together with its attached oxygen atom forms a hydrolyzable ester protecting group; comprising dehydrating in an organic solvent a cyclohexene compound of the formula:

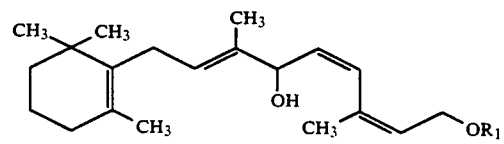

wherein $R_1$ is as above; in the presence of a catalyst selected from the group consisting of an alkaline earth metal bromide, manganese bromide and hydrates thereof, and optionally in the presence of an amino acid hydrobromide.

10. The process of claim 9, wherein the catalyst is calcium bromide, calcium bromide dihydrate, magnesium bromide, magnesium bromide hexahydrate or manganese bromide.

11. The process of claim 9, wherein the solvent is acetonitrile, acetone or isopropenyl acetate.

12. The process of claim 9, wherein the amount of catalyst used is 4 to 40 mol percent based on the amount of compound to the dehydrated.

13. The process of claim 9, wherein the dehydration is carried out in the temperature range of $-20°$ C. to $50°$ C.

14. The process of claim 9, wherein the dehydration is carried out in the presence of the amino acid hydrobromide $\beta$-alanine hydrobromide.

15. The process of claim 14, wherein the amount of $\beta$-alanine hydrobromide is 1 to 4 mol percent based on the amount of said cyclohexene.

16. The process of claim 9, wherein the dehydration is effected in the presence of about 40 mol percent of calcium bromide dihydrate in acetonitrile together with a trace of acetic acid at about $0°$ C.

17. The process of claim 9, wherein 1-(9-acetoxy-3,7-dimethyl-4-hydroxy-nona-2,5,7-trienyl)-2,6,6-trimethyl-cyclohexene is dehydrated in the presence of calcium bromide dihydrate and $\beta$-alanine hydrobromide in a molar ratio of about 1:1 in acetonitrile at about $0°$ C.

18. A process of claim 9, wherein 1-(9-acetoxy-3,7-dimethyl-4-hydroxy-nona-2,5,7-trienyl)-2,6,6-trimethyl-cyclohexene is dehydrated in the presence of calcium bromide dihydrate and $\beta$-alanine hydrobromide in a molar ratio of about 1:1 in acetone at room temperature.

* * * * *